Figure 3A:
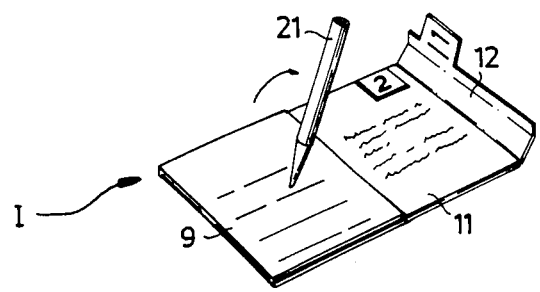
Figure 3B:
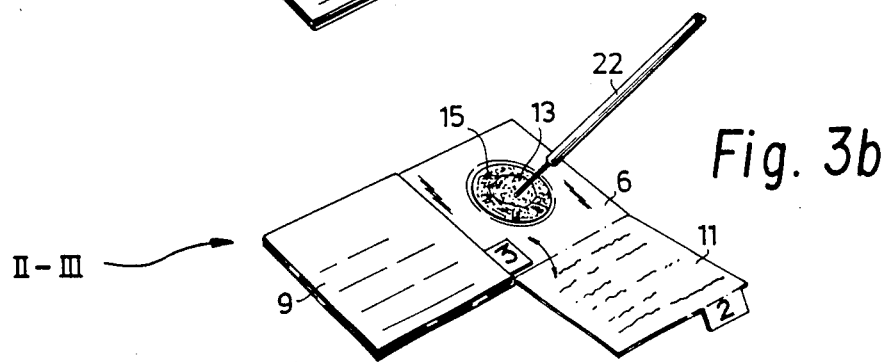
Figure 3C:
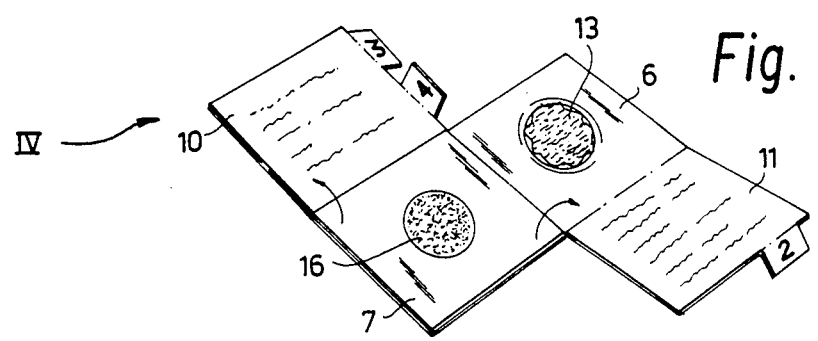
Figure 3D:
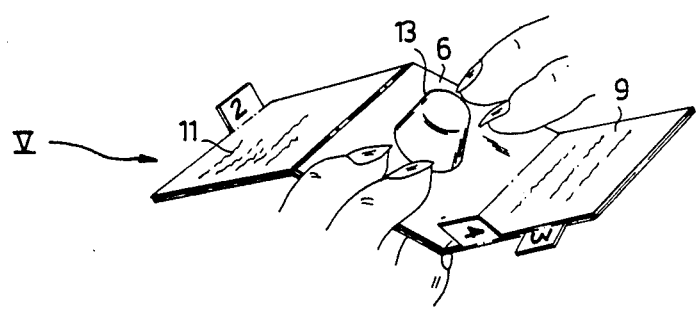

United States Patent [19]

Swanljung

[11] Patent Number: 4,717,656

[45] Date of Patent: Jan. 5, 1988

[54] DEVICE FOR CHEMICAL ANALYSES AND USE THEREOF

[75] Inventor: Carl G. P. Swanljung, Trångsund, Sweden

[73] Assignee: Vertrik Bioteknik AB, Trångsund, Sweden

[21] Appl. No.: 740,065

[22] PCT Filed: Nov. 30, 1984

[86] PCT No.: PCT/SE84/00409

§ 371 Date: May 23, 1985

§ 102(e) Date: May 23, 1985

[87] PCT Pub. No.: WO85/02466

PCT Pub. Date: Jun. 6, 1985

[30] Foreign Application Priority Data

Dec. 2, 1983 [SE] Sweden ............... 8306666
Jul. 27, 1984 [SE] Sweden ............... 8403883

[51] Int. Cl.⁴ .............................................. G01N 31/22
[52] U.S. Cl. ........................................ 435/7; 422/56; 422/57; 422/58; 435/805
[58] Field of Search .................. 422/55, 56, 57, 58, 422/61; 435/805, 7

[56] References Cited

U.S. PATENT DOCUMENTS

| | | | |
|---|---|---|---|
| 3,194,963 | 7/1965 | McKee | 436/905 X |
| 3,511,608 | 5/1970 | Anderson | 422/56 |
| 3,644,177 | 2/1972 | Zyk | 435/805 X |
| 3,689,224 | 9/1972 | Agnew et al. | 435/810 X |
| 3,936,357 | 2/1976 | Milligan et al. | 435/287 |
| 3,992,158 | 11/1976 | Przybylowicz | 422/58 X |
| 4,055,394 | 10/1977 | Friedman et al. | 422/56 |
| 4,066,403 | 1/1978 | Bruschi | 422/57 X |
| 4,108,729 | 8/1978 | Mennen | 422/56 X |
| 4,365,970 | 12/1982 | Lawrence et al. | 436/66 |
| 4,645,743 | 2/1987 | Baker et al. | 422/58 X |

FOREIGN PATENT DOCUMENTS

| | | |
|---|---|---|
| 0051183 | 5/1982 | European Pat. Off. |
| 0064392 | 11/1982 | European Pat. Off. |
| 8205751-4 | 10/1982 | Sweden |

*Primary Examiner*—Barry S. Richman
*Assistant Examiner*—Jill Johnston
*Attorney, Agent, or Firm*—Burns, Doane, Swecker & Mathis

[57] ABSTRACT

The device according to the invention intended for chemical analyses comprises a continuous sheet with at least two segments (6,8 or 30,31). The first one of the segments (6 or 30) contains a site (13 or 35) on which at least one of the reagents is present from the beginning and on which the contact between sample and reagent can take place. A second segment (8 or 31) contains a site (17 or 39) on which the presence of detectable substance can be shown. The first and other segments (6 and 8 or 30 and 31) are foldable in such a way that the site (13 or 35) with the reagent can be brought to overlap the site (17 or 39) for detection. The device also includes at least one arrangement (7 or 48) for the separation of reagent that has not reacted during the contact between sample and reagent. This arrangement is activated before the presence of detectable substance is shown. The segments are foldable in such a way that the desired segments can overlap each other for performing the desired analytical steps.

The use according to the invention relates to the use of the device for chemical analyses, especially within the fields of medicine and agriculture, e.g. immuno-chemical analyses, such as enzyme immuno assay, fluorescence immuno assay and luminescence immuno assay.

29 Claims, 24 Drawing Figures

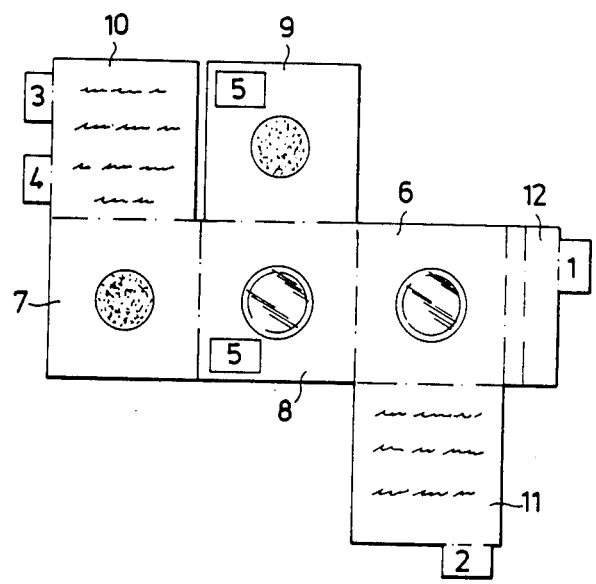
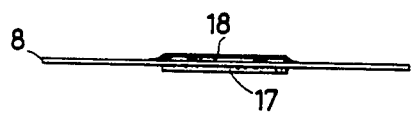
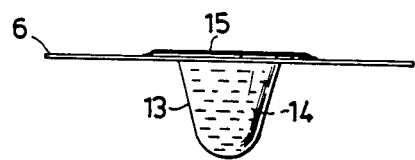
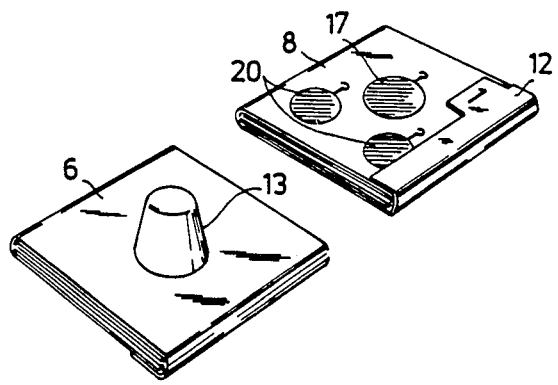

Fig. 4a
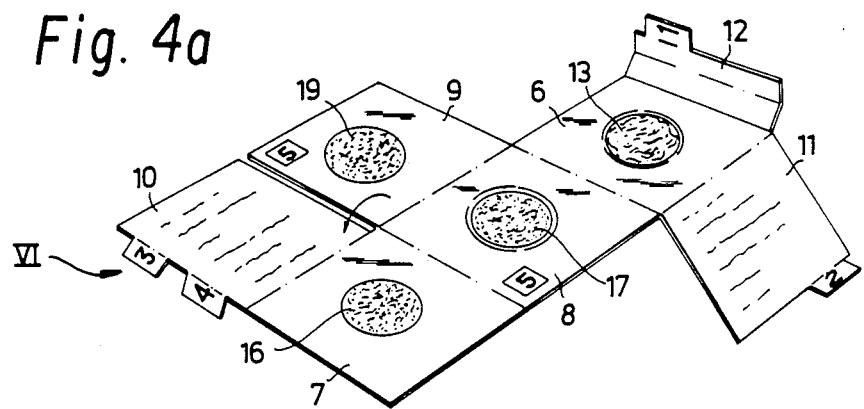
Fig. 4b
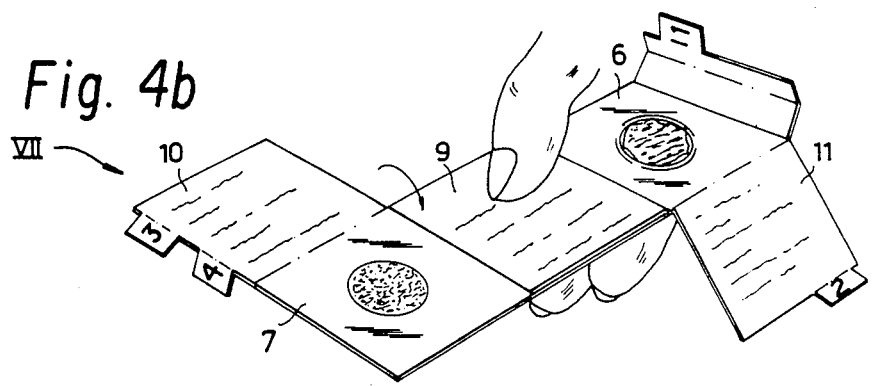
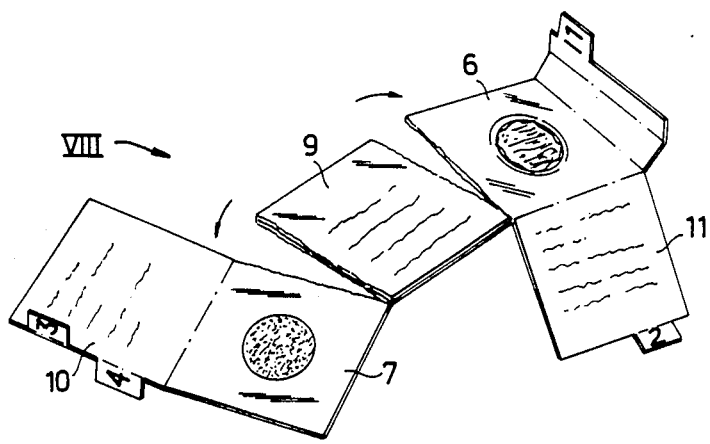
Fig. 4c
FIG. 4d
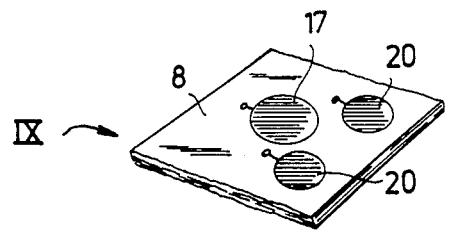

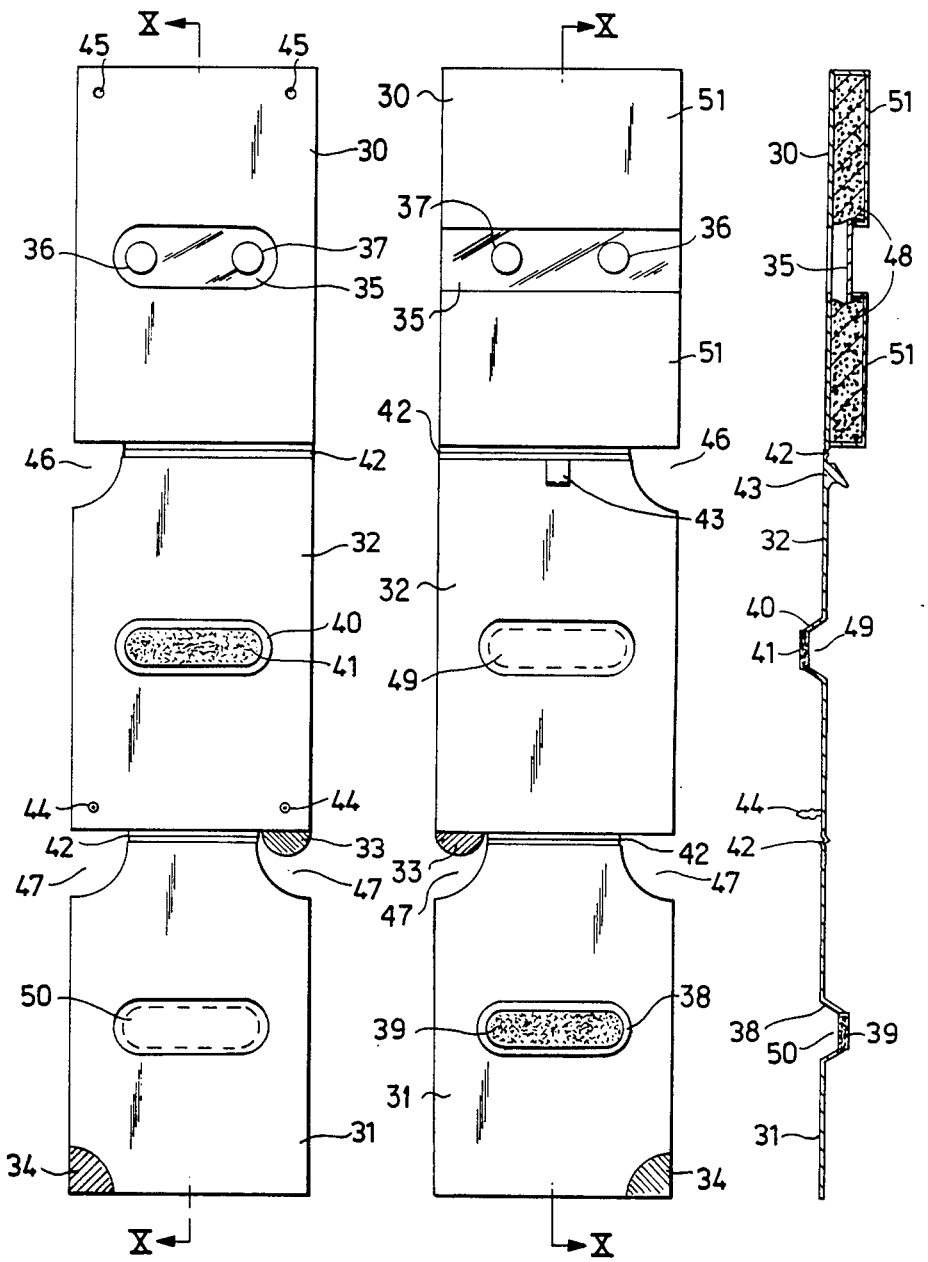

DEVICE FOR CHEMICAL ANALYSES AND USE THEREOF

TECHNICAL FIELD

The present invention relates to the field of chemical analyses and more specifically to a device for performing such as well as to a use of said device. Analyses to which the present invention is applicable are such, wherein the sample to be tested is contacted with reagent(s) reacting with the sample to form a detectable substance, which in turn is detected for a qualitative or a quantitative determination thereof. The invention is especially interesting within the field of medicine, e.g. immuno-chemical analyses, but is not limited thereto as the basic idea of the invention is applicable to a variety of analyses of the kind referred to above.

BACKGROUND OF THE INVENTION

In immuno-chemical analyses, such as enzyme immuno assay (EIA) or fluorescence immuno assay (FIA), free labelled antibody or antigen must in most cases be separated from the labelled antigen-antibody complex. This is commonly accomplished by means of a solid phase that can be present e.g. in the form of a particle or a surface, either the free labelled component or the complex being retained by the solid phase on the basis of molecular size, adsorption or different types of chemical (including immuno-chemical) bonding. Typical for such analyses today is that they require several liquid processing steps for carrying out the reaction sequence. For that reason most immuno-chemical analyses are, with the technique used today, limited to laboratories having trained personnel.

By means of the device according to the invention it has been shown to be possible to considerably facilitate and simplify the processing and operational steps of analyses of the above-mentioned type so that they can be performed also by non-trained personnel, e.g. doctors and nurses in offices and hospitals. The device is even simple enough to be handled in many cases by the patient himself. Furthermore, an important factor in the last-mentioned connection is that due to its very simple construction the device can also be made very inexpensively, which means that it might achieve a wide spread commercial use, at least for some qualitative and semi-quantitative tests where certain states of illness can be confirmed by the patient himself before there is a need for any consultation with a doctor.

However, as was mentioned above the device is in no way limited to use in connection with immuno-chemical analyses, but for the sake of simplicity and for a better understanding it will still be described more in detail below in connection therewith. In this context it could also be added that the described analyses and the reagents utilized in connection therewith are well known and are disclosed in numerous references. Thus it should not be necessary to repeat details thereabout here since these can be found in suitable literature within the field. For examples of techniques used within the field of immuno-chemical analyses reference is made to the techniques described in Swedish Patent Application Ser. No. 8205751-4. However, nor is said literature reference intended to be in an way exhaustive within this field.

For the purpose of elucidating the invention even more as well as the technical field to which it relates it should also be added that it bears no relation to those numerous simple diffusion devices which are disclosed in the literature, i.e. where a sample either passively or by means of capillary forces is allowed to diffuse through one or more chemically active layers. Examples of references which disclose devices of this kind are U.S. Pat. No. 3,511,608, GB Pat. No. 2,031,583, EP No. 64,392, U.S. Pat. No. 4,066,403 and EP No. 51,183. As far as these are concerned it should be pointed out that those overlapping segments which are disclosed in U.S. Pat. No. 3,511,608 or those foldable sheets which are disclosed in GB Pat. No. 2,031,583 and EP No. 64,392 relate to possible manufacturing methods for diffusion devices but have no functional purpose for the execution of the analysis, during which time said segments or sheets are permanently connected to one another in one single piece. Although there in e.g. GB Pat. No. 2,031,583 and EP No. 64,392 are flaps which are foldable to the user, these flaps are only used as protective lids or covers and do not take part in the chemical or analytical process.

The device according to the invention differs essentially from the above-mentioned devices through the fact that it is not based upon any diffusion principle. Instead the analysis is performed step by step as in the laboratory. The novelty of the concept is that liquid samples and reagents need not be transferred between test tubes or test cups by repeated pipetting operations. Instead samples, reagents and even a washing function are contained on surfaces of the device. Transfer of samples or reagents between the surfaces is accomplished by a simple folding action. This offers considerable advantages over multilayer diffusion elements of the type that are disclosed in e.g. U.S. Pat. No. 4,066,403 and EP No. 51,183. The user retains full control of the timing of the different reaction steps, while the timing for diffusion devices of the multilayer type can be varied only by the manufacturer by choice of layer material and even then merely to a limited extent. Moreover, the device according to the invention can be utilized for the analysis of most substances without a need for any major modifications of its basic structure or design. In immuno-chemical analyses there are substances of extremely varying size, from drugs having a molecular weight of not more than 500 to whole cells and bacteria which are a billion times larger. As substances of different size diffuse at different rates, diffusion devices therefore have an additional drawback in that it is necessary to adjust the types of layers for each kind of analyte. Finally, it should be added that the method of manufacture and the storage properties of the device according to the invention are based on established technology while these factors have proven to be difficult to master in practice for immuno-chemical diffusion devices of the multilayer type.

DISCLOSURE OF THE INVENTION

The device according to the invention can briefly be described as a complete test kit for performing an analysis of the above-mentioned type wherein all chemically active parts which are necessary for carrying out the analysis are built into the device, i.e. there is no need to perform any stage of the analysis outside the device per se. These chemically active parts are arranged or mounted in such a way that they are contacted with the sample and each other by a simple folding system. Furthermore, said folding system can be made completely self-instructing i.e. instructions for performing the analysis may be included within the folding system and it is also possible to include a number of numbered or color-coded tabs as part of the folding system, which tabs give stepwise directions for the operational sequence. In addition thereto the device also includes as an integral part a result display which for instance in the form of a color or fluorescence gives a positive, negative or optionally quantitative response. In other words, all necessary reagents and reaction steps can be built into a very simple, compact and inexpensive construction, which offers hitherto unrealized opportunities, especially within the field of medicine.

More specifically, the device according to the invention is characterized in that it comprises a continuous sheet having two or more segments, the first of which contains a site where the contact between sample and reagent can take place, and a second one contains a site where the presence of a desired detectable substance can be shown, the segments being foldable in such a way that they can overlap each other as desired in order to accomplish the required reactions. The site on the first segment preferably contains the designated reagent initially, i.e. said reagent is present or included in the device so that it need not be prepared before the analysis in question can be started. This is applicable also to the detecting reagent on the second segment, i.e. also this reagent can, if required, be present in the device from the beginning.

Characteristic of the invention is also that the device also includes at least one arrangement for the separation of excess reagent, i.e. reagent that has not reacted during the contact between e.g. sample and reagent(s), said arrangement being placed so as to be able to exercise its function before the presence of detectable substance is shown.

In other words the basic idea of the present invention is a number of segments with incorporated reagents which segments are connected to each other into one continuous structure and in such a way that they can be folded so that desired reagents come into contact with each other. While the simplest and accordingly the most inexpensive construction would be one where said sheet is represented by one single piece, e.g. in the form of a paper sheet or plastics sheet with folding lines, along which the given segments can be folded on top of each other, the term "continuous sheet" is intended to mean any construction where the different segments are connected to each other. Thus, the invention can of course also be applied by manufacturing separate segments, which segments are then linked to each other by means of a linking mechanism of the hinge type or similar. Such more sophisticated devices should be applicable primarily to devices which are intended to be used several times, e.g. by using such sites containing chemical reagents which are easily exchangeable, but in many cases the device is intended for disposal after use and in these cases a simple foldable material should be preferable for economical reasons.

Often analyses of the type referred to include a step where one or more components or reactants are to be separated from the other components or reactants before detection can or should be started. For instance this is applicable to the separation of a liquid from a solid phase (solid phase reagent or a solid phase formed by the reaction). Particularly for these types of analyses the device according to the invention has turned out to be especially interesting, since also this separation operation is built in the very compact and easy to operate device. The only reagent or accessory which may possibly need to be added externally is a washing liquid which it may be preferable to handle separately for practical purposes, especially since this washing liquid is often chemically stable and in many cases even consists of ordinary water. Nor does the utilization of a washing liquid require any exactness contrary to what is generally the case with reagents.

The separation arrangement can for instance be a third segment provided with a separation element or medium, which segment is arranged or mounted to be folded in between the above-mentioned first and second segments respectively to accomplish the desired separation. As to such a separation arrangement it should be noted that, as is the case also for the other reagents used, it is chosen completely in conformity with prior art. In many cases it should be possible simply to utilize a filter paper to obtain the desired function, which of course also keeps the price down.

According to another preferable embodiment of the invention the arrangement for separation of the reagent is one or more separation or absorption media arranged adjacent to the site on the first segment. In other words no extra segment is utilized in this case but said arrangement is included in the segment on which the contact between sample and reagent takes place. The fact that said media are arranged adjacent to said site on the first segment in principle means that they should be able to be activated merely by application of liquid, i.e. generally washing liquid in an amount exceeding the volume that is used for the application of the sample. In other words liquid will automatically be sucked up by the absorbing medium. This can be accomplished by arranging an absorbing material in at least one well or container in the first segment, which well or container has an opening allowing an inflow of liquid from the site on the first segment.

In some cases the analysis comprises of reactions in several steps before the detection can be performed. In spite of its simplicity the device according to the invention is useful also in such cases, viz. by simply including therein further segments which contain the desired reagent(s) and which are mounted to be folded in any suitable sequence to accomplish a reaction with the sample or with a reaction product formed in any preceding step.

Another embodiment of the device according to the invention is a device which contains an extra segment merely intended for the application of the test sample or for a dilution thereof before it is folded by means of said extra segment into contact with a reagent on another segment.

Still another embodiment of the device according to the invention is a device wherein the detecting reagent is a color-forming reagent and wherein one of the segments contains one or more windows with reference color or colors. with which the color formed can be directly compared for an evaluation of the analysis. In other words the device has previously been provided with one or more colors which give a direct qualitative or quantitative measure of the substance to be detected and with which the color formed at the analysis can be compared. Preferably said window(s) is (are) of course arranged on the same segment where the color formed at the analysis develops so that those colors or shades to be compared are immediately adjacent each other.

Last-mentioned embodiment directly enables a visual reading and even if such a visual reading can be made with great accuracy it can some times be desirable to detect the color optically. The device according to the invention can of course also be constructed for this purpose so as to be able to be directly inserted into or on an instrument for an optical reading of the color developed. Also other detecting reagents than those which develop colors may be utilized and in such cases prior art is followed. Thus it should not be necessary to go into greater detail here. However, as examples thereof fluorescence and luminescence may be mentioned.

In some cases it can be desirable to stop the detecting reaction used in the analysis, e.g. after a certain predetermined time, in order to make an exact comparison between the formed color and reference colors, and in such a case it is possible to provide the device with an extra segment fitted with a site that contains an inhibitor for the utilized detecting reaction. This segment is then arranged so as to be able to be folded into contact with the segment on which the detecting reaction takes place, to inhibit or stop the detecting reaction.

An interesting application of the device according to the invention is represented by the case where the analysis includes a separation of a fluid phase, commonly a liquid phase, from a solid phase and a detection of a substance in the fluid phase. A preferred device in such a case is characterized in that the site on the first segment comprises of a container wherein the sample is intended to be applied to react with a solid phase reagent present in the container or alternatively to react to the formation of a solid phase, that the site on the second segment contains detecting reagent for the desired substance of the fluid phase, and that a third segment containing a separation arrangement that enables a passage of the fluid phase but not of the solid phase, is placed to be folded in between the container on the first segment and the detection site on the second segment. Thus, in this case, when inverting the device the fluid phase and thereby the substance to be detected will come into contact with the detecting reagent without having any interference from the solid phase upon the detecting reaction.

In order to store the reagent in the container of the first segment protected from external influence before the sample is applied, the opening of the container is preferably covered by some type of protecting layer, e.g. a foil, which keeps the reagent in place prior to the application of the sample.

Another interesting application of the device according to the invention is its use in an enzyme immuno assay based on antigen-antibody reactions and wherein the device is characterized by a first segment having a site made of a transparent plastic for the application of the sample and preferably also a second site for a control sample, the plastic being prepared with reagent in the form of antibody or antigen fixed thereto. Such a fixation of antigens or antibodies to plastic surfaces is well known and described in literature, see e.g. IMMUNOENZYMATIC TECHNIQUES (edited by S. Avrameas, P. Druet, R. Massayeff and G. Feldman) Elsevier Science Publishers, Amsterdam/New York/Oxford, 1983. The device is further characterized by a second segment having a site with detecting reagent in the form of a chromogenic enzyme substrate, a third segment provided with a site with an absorbent pad with soluble, optionally lyophilized enzyme-labelled antibody or antigen, said third segment being arranged to be folded to overlap the first segment before the second segment is folded to overlap said first segment. Furthermore, the device contains a separation arrangement in the form of absorbing material placed in at least one well on the first segment in such a way that when washing liquid is applied onto the transparent plastic of the first segment to wash away unreacted reagent before the second segment is folded to overlap the first one, said washing solution is automatically absorbed by said absorbing material.

As was mentioned above numeral functions can be built into the device according to the invention. Thus, it can also be provided with one or more further segments, which are of another kind than the previously described, chemically active parts. Examples of such interesting devices according to the invention is a device characterized in that it includes one or more further segments with instructions relating to the operational handling of the device and/or patient data or similar, which segments are also foldable in such a way that the segments can overlap each other in the desired sequence, or a device characterized by segments providing a closing mechanism that can be folded to seal the package.

In order to further build up or improve the self-instructing folding system, so as to eliminate to a very great extent the risks of an erroneous operation thereof, another interesting device according to the invention can be characterized by numbered or color-coded tabs which step by step give directions as to the order of opening the segments. The device can also be designed so as to be characterized by certain segment(s) that may be torn off so that they can be removed from the device after having been utilized. For instance it may be suitable to retain only that or those segment(s) on which the result of the analysis is read and on which optionally also data concerning e.g. patient identification, type of test, time or serial number are present or have been noted.

As concerns the foldability of the segments and the overlappings of the different segments the device according to the invention is preferably designed in such a way that the segments can be folded to essentially overlap each other. That is, all segments are from the beginning, i.e. with the device ready for use, folded so as to be on top of each other in any suitable order in one single pile. In this way the final package has a very compact shape, i.e. the shape of a match box with a foldable cover.

Moreover, the invention relates to use of the device described above for chemical analyses in general and especially within the fields of medicine and agriculture. A preferable use in this connection is in immuno-chemical analyses, e.g. for enzyme immuno assay, fluorescence immuno assay and luminescence immuno assay, and analyses wherein hybridization reactions between nucleic acids are used.

DRAWINGS

Figure 6A:
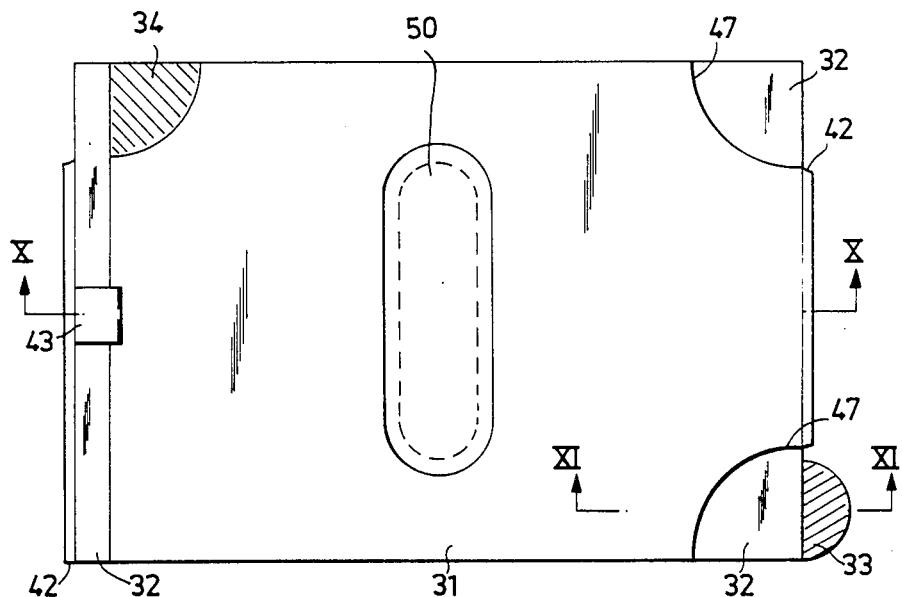
Figure 6B:
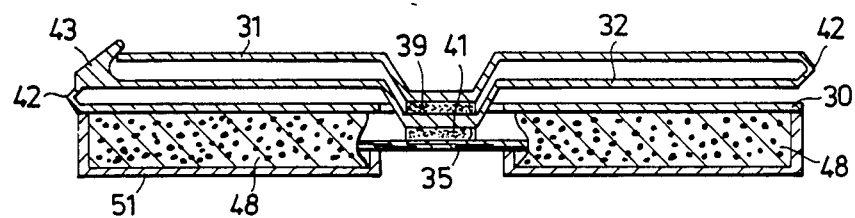
Figure 6C:
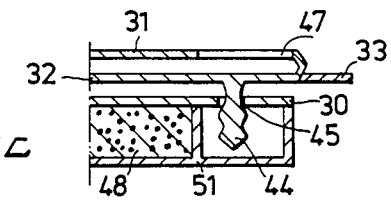
Figure 7A:
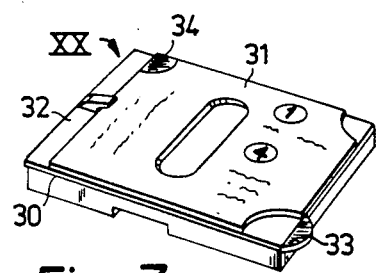
Figure 7B:
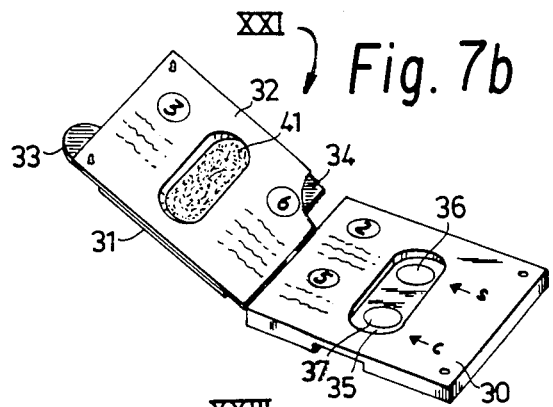
Figure 7C:
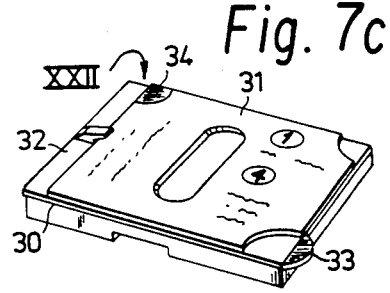
Figure 7D:
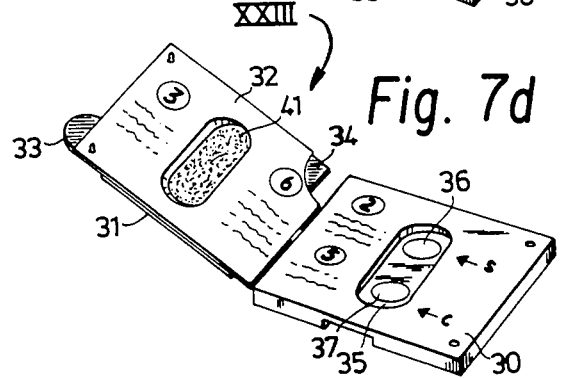
Figure 7E:
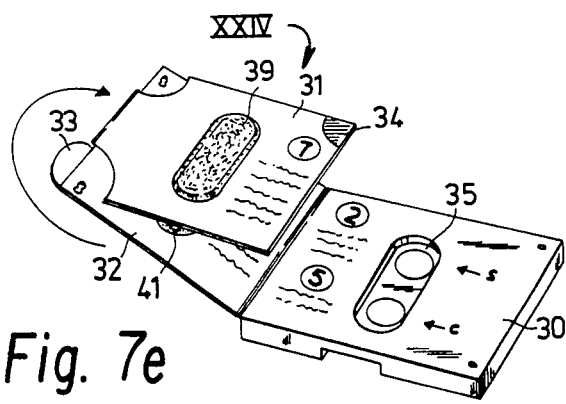
Figure 7F:
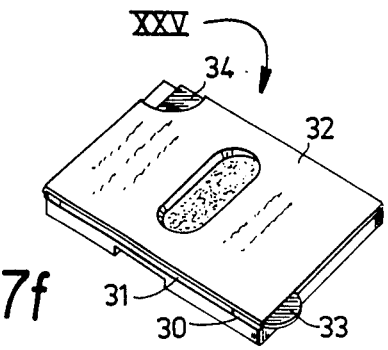
Figure 7G:
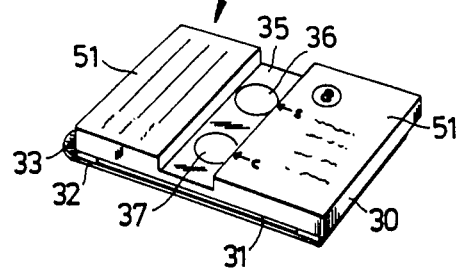

The device according to the invention will now be described more in detail in connection with the accompanying drawings which show two preferable embodiments of the device. Thus, in the drawings:

FIG. 1a shows a top view of a device containing six segments and wherein the separation means is represented by a special segment, FIG. 1b is a side view showing four of the segments from FIG. 1a, FIG. 2 shows the device from FIG. 1a in the folded state and seen from above and from below, respectively, FIGS. 3a–d and 4a–d show the analysis sequence when using the device according to FIG. 1a for enzyme immuno analysis, FIG. 5a shows a top view of a second device containing three segments and wherein the separation means is present on the first segment, FIG. 5b shows a bottom view of the device according to FIG. 5a, FIG. 5c shows a side view of the device according to FIG. 5a along an imagined cross sectional line X—X, FIG. 6a shows the device from FIG. 5a in a folded state seen from above and in a magnified scale of 2:1, FIG. 6b shows a side view of the device from FIG. 5a in a folded state along an imagined cross sectional line X—X and in a magnified scale of 2:1, FIG. 6c shows a side view of the device from FIG. 5a in a folded state along an imagined partial cross sectional line XI—XI and in a magnified scale of 2:1, FIGS. 7a–g shows the analysis sequence when utilizing the device according to FIG. 5a for enzyme immuno analysis.

The device shown in FIG. 1 comprises a continuous sheet having six segments 6–11, of which segments 6–9 show chemically active sites, while segments 10 and 11 represent logistic auxiliary segments for the chemical operation. Furthermore, some of the segments are provided with tabs numbered 1–5 intended to show the sequence for the opening of the device. Finally, the Figure shows a smaller foldable segment 12 intended for sealing the device.

More specifically the segment 6 comprises a reaction container 13 containing a solid phase reagent 14 and covered by a foil 15. The segment 7 is provided with an area 16 that is a filter paper, while the segment 8 contains a chemically active surface 17 in the form of a enzyme substrate and a protecting, transparent plastic foil 18. The segment 9 in turn has a chemically active surface 19 in the form of an enzyme inhibitor.

As was mentioned above FIG. 2 shows the device in a folded state and seen from below and above, respectively, the reference numerals being the same as in FIG. 1. However, FIG. 2 also shows two color reagent windows 20 with which the color of surface 17 formed at the analysis can be compared.

As concerns the handling of the device shown reference is made to FIGS. 3a–d and 4a–d, wherein sequences numbered I-IX are shown, which sequences can be described as follows.

I. The kit or package is broken and opened by tab 1. The name as well as the data of the patient can be noted where indicated by means of a pen 21.

II. Tab 2 is opened. The sample is added to the reaction container 13 by means of a test stick 22 by which the foil 15 is punched. The sample is mixed into the reaction mixture 14 with the test stick. Then the sample is allowed to incubate for a suitable time. Flap 2 can then be resealed, if desired.

III. After the incubation tab 2 is reopened if it has been sealed.

IV. Tab 3 is opened whereby the filter paper surface 16 is exposed, and below said surface there is an enzyme substrate surface 17. The segment with the filter paper 16 is then folded over the reagent container 13.

V. The device is inverted momentarily.

VI. Then tab 4 is opened which exposes the enzyme substrate surface 17 and the enzyme inhibitor surface 19.

VII. The surface 19 is folded so as to cover surface 17 by means of tab 5 in order to stop the optional enzyme reaction. After the folding these surfaces remain adhered to each other as they are in the case shown provided with an adhesive of the type that enables an opening and a resealing operation.

VIII. The other segments can now be torn or stripped off. On the two remaining segments which adhere to each other the name and data of the patient may be found.

IX. Through the window on the opposite side of the remaining segments the color reaction obtained is read by a comparison with the reference colors in window 20.

As concerns the exemplified reaction the color reaction is dependent on the amount of enzyme which has not been taken up by the solid phase 14 in the reaction container 13. Thus, the reaction system of the reaction container 13 has such a composition that the amount of enzyme taken up by the solid phase 14 is directly dependent on the presence of antigen or antibody, respectively, in the sample. At the inversion of FIG. 3, step V, the sample is filtered through the filter paper 16 which prevents the solid phase 14 of reaching the enzyme substrate surface 17.

The device shown in FIGS. 5 and 6 shows three segments 30–32 which all take active part in the analytical process. Furthermore, segments 31 and 32 are provided with color coded tabs 33 and 34 to show the sequence of opening the device.

The segment 30 contains a transparent plastic surface 35 to which an antibody (or antigen) is chemically or physically fixed. On the plastic surface 35 there is a spot 36 marked for a sample and a spot 37 marked for a control or standard. Around the plastic surface 35 there is a built-in separation arrangement in the form of absorbent media 48 in wells on the bottom plate 51.

The segment 31 contains a well 50, on the opposite convex side 38 of which there is attached an absorbent pad 39 which contains a chromogenic enzyme substrate. In the corresponding way there is a rise in the segment 32 on the upper convex side 40 to which is attached an absorbent pad 41 which contains an enzyme-labelled antibody (or antigen). As concerns pads 39 and 41 they are arranged so as to each overlap the plastic surface 35 by a suitable folding of the segment 31 or 32, respectively. The pad which is not in operation rests in the concave recess (49 or 50, respectively) that has been formed on the opposite side of the other pad.

The folding of the segments is facilitated by folding lines 42. At the folded starting position shown in FIG. 6 the segment 31 is folded against the bottom side of segment 32, it being locked by a snapping lock 43. The segment 32 is in turn folded against segment 30, it being locked by those two locking pins 44 which are reversibly locked in wells 45 of segment 30. The indentation 46 of segment 32 enables the grasping of tab 34 when segment 31 is opened, while the indentation 47 also enables a folding of segment 31 against the top side of segment 32 with a retained possibility of folding and locking segment 32 against segment 30 with the locking pins 44.

As concerns the operation of the device shown in FIGS. 5–6 reference is made to FIGS. 7a–g in which sequences numbered XX-XXVI are marked, which sequences can be described as follows:

XX. The package is opened by tab 33. If desired, name and data of the patient can be noted on the back side of the package.

XXI. The sample is applied to the spot 36 on the surface 35. If the sample is liquid, this can be accomplished e.g. by applying a drop of sample on the surface. In the corresponding way a control or standard is applied to spot 37. If the substance to be tested is present in the sample, control or standard it reacts with and is bound to the antibody (or antigen) which is fixed to the plastic surface 35.

XXII. The package is resealed. Thereby a second analysis step is started. If the substance to be tested is present it now reacts also with and is bound to the soluble, enzyme-labelled antibody (or antigen) which is present in the absorbent pad 41. Thereby this enzyme-labelled antibody will also be indirectly bound to the plastic surface 35 by the previous and still continuing reaction of step XXI.

XXIII. After a suitable reaction time the package is reopened by tab 33. Washing liquid is now dropped onto surface 35 which is thereby washed free from soluble, enzyme-labelled antibody that has not reacted with the tested substance.

XXIV. By means of tab 34 segment 31 is now opened and folded on top of segment 32.

XXV. The package is resealed. Thereby the detecting reaction is started. Enzyme-labelled antibody that has reacted in the first reaction step transforms the chromogenic enzyme substrate on the absorbent pad 39 into a colored substance.

XXVI. After the proper reaction time the result is read on the back side of the package through the transparent plastic surface 35. The color formed on the test spot 36 is compared with the result of the control reaction on spot 37 or with reference colors.

As concerns the exemplified analytical sequence it may further be added that the color reaction is directly dependent on the amount of enzyme that is present on the surface 35 after the washing step XXIII. This amount is in turn directly dependent on the presence of the tested substance in the sample which is able to bind enzyme-labelled antibody (or antigen) and is at the same time bound to antibody (antigen) fixed on the surface 35.

EXAMPLES

The following working examples are intended to elucidate the device according to the invention more in detail. These examples describe the application of the device to the determination of a small as well as a very large protein and a virus.

For all applications a device according to FIGS. 5-6 in a scale 1:1 was used. The segments 30-32 were manufactured from polyvinyl chloride (PVC). The transparent plastic surface 35 consisted of a rectangular slide made of immunograde polystyrene (Nunc A/S, Roskilde, Denmark), with marked circular spots 36 and 38 on the surface. Antibody was fixed to these spots as will be described for each type of application.

The absorbing material 38 of the separation arrangement was manufactured from cellulose sponge (Wettex®, Celloplast AB, Norrköping, Sweden). For the absorbent pads 39 and 41, Whatman® 3MM filter paper (Whatman Ltd., Maidstone, Kent, U.K.) was used. These filter paper pads were impregnated with reagents as will be described for each type of application.

For the assay of thyroglobulin the device was fitted with an extra segment, the sole purpose of which was to provide a cover for surface 35, to prevent evaporation of the sample.

Assay for human chorionic gonadotropin

Human chorionic gonadotropin (hCG is a small protein with a molecular weight of approx. 46 000). The assay is useful in the diagnosis of pregnancy.

Preparation of the device

Antibody was fixed to the plastic slide 35 by applying 75 μl of monoclonal anti-alpha subunit of hCG antibody (clone 5503, Oy Medix Ab, Kauniainen, Finland) in a concentration of 10 μg/ml diluent, to each of spots 36 and 37. The diluent (abbreviated PBS) was 0.05 mol/l sodium phosphate, 0.15 mol/l NaCl, pH 7.2. The slides were incubated in a humidity chamber for 18 h at 4° C. They were then rinsed with approx. 10 ml washing solution (abbreviated PBS-Tween), consisting of 0.05% Tween®-20 (Merck, Hohenbrunn, Germany) in PBS. Thereafter the slides were submerged in a dish containing a solution (abbreviated PBS-BSA) consisting of 1% w/v bovine serum albumin (Sigma Chemical Co., St. Louis, Mo., U.S.A.) in PBS and incubated 90 min at room temperature. Subsequently the slides were again rinsed with approx. 10 ml PBS-Tween, followed by 10 ml distilled water and left to dry.

The absorbent pad 41 was impregnated with a solution of peroxidase conjugated monoclonal anti-beta subunit of hCG antibody (Sensi-Chrome ™ Conjugate Reagent, Hoffman-La Roche Inc., Nutley, N.J., U.S.A.), undiluted. The absorbent pad 39 was impregnated with a chromogenic substrate solution of 0.42 mmol/l 3,3',5,5'-tetramethylbenzidine, (Miles Laboratories, Inc., Elkhart, Ind., U.S.A.), 1.4 mmol/l urea peroxide in 0.1 mol/l sodium acetate/citric acid buffer, pH 6.0, prepared as described by E. S. Bos et al. (1981), J. Immunoassay 2, 187.

Execution of the assay

The assay was performed essentially as illustrated in FIG. 7 with sequence XX-XXVI. However, the following details of samples, volumes, times and other conditions may be added.

As samples for the assay, Lyphochek® I and II human control urines (Bio-Rad Laboratories, Inc., Anaheim, Calif., U.S.A.) with stated hCG concentrations of 3,900 and 550 international units per liter, respectively, were used. These samples were further diluted with a known negative urine sample 1:2, 1:4, 1:8 and 1:16. The known negative urine sample was used as a blank.

The device was opened and 1 drop of approx. 50 μl of each sample was applied to spot 36 and the same volume of blank to spot 37. The device was then closed by folding segment 32 upon segment 30 to transfer the conjugated antibody in absorbent pad 41 into the plastic surface 35. The device was left closed and incubated for 15 min. at room temperature.

The device was then reopened to expose surface 35, which was washed with approx. 1 ml PBS-Tween. Segment 31 was then folded onto segment 30 to transfer the chromogenic substrate in absorbent pad 39 onto plastic surface 35. The device was again left closed and incubated for 5 min. at room temperature. The color reaction was then immediately read on the back of the device through the transparent plastic at spots 36 and 37. A faint blue color was designated "+", a distinct blue color "++" and a strong blue color "+++". The assay results were compared to a commercially available pregnancy test, Sensi-Chrom ™ (Hoffman-La Roche Inc., Nutley, N.J., U.S.A.), run simultaneously in test tubes.

Results

| Sample | Device according to the invention | Sensi-Chrome ™ procedure |
|---|---|---|
| Known negative urine sample | − | − |
| Lyphochek ® II 1:16 | + | − |
| Lyphochek ® II 1:8 | + | + |
| Lyphochek ® II 1:4 | ++ | ++ |
| Lyphochek ® II 1:2 | +++ | +++ |
| Lyphochek ® II | +++ | +++ |
| Lyphochek ® I | +++ | +++ |

As can be seen, there was a good correlation between the procedures.

Assay for human thyroglobulin

Human thyroglobulin is a relatively large protein with a molecular weight of approx. 660,000. The assay is useful in the monitoring of thyroid cancer.

Preparation of the device

Antibody was fixed to the plastic slide 35 by applying 75 μl of monoclonal anti-human thyroglobulin antibody (clone TF-33, Novo Industri A/S, Bagsvaerd, Denmark) in a concentration of 10 μg/ml diluent, to each of spots 36 and 37. The diluent (abbreviated PBS) was 0.05 mol/l sodium phosphate, 0.15 mol/l NaCl, pH 7.2. The slides were incubated in a humidity chamber for 18 h at 4° C. They were then rinsed with approx. 25 ml washing solution (abbreviated PBS-Tween), consisting of 0.05% Tween ®-20 (Merck, Hohenbrunn, Germany) in PBS. Thereafter the slides were submerged in a dish containing a solution (abbreviated PBS-BSA) consisting of 1% w/v bovine serum albumin (Sigman Chemical Co., St. Louis, Mo., U.S.A.) in PBS-Tween and incubated 45 min at room temperature. Subsequently the slides were again rinsed with approx 25 ml PBS-Tween, followed by 25 ml distilled water and finally dried under a flow of compressed air.

The absorbent pad 41 was impregnated with a solution of peroxidase conjugated rabbit anti-human thyroglobulin (Dakopatts A/S, Glostrup, Denmark), diluted 1:500 in PBS-BSA. The absorbent pad 39 was impregnated with a chromogenic substrate solution of 0.05% w/v ortho-phenylene diamine (Sigma Chemical Co., St. Louis, Mo., U.S.A.), 0.01% v/v $H_2O_2$ in 0.06 mol/l sodium phosphate, 0.03 mol/l sodium citrate, pH 5.0.

Execution of the assay

The assay was performed essentially as illustrated in FIG. 7 with sequences XX–XXVI. However, the following details of samples, volumes, times and other conditions may be added.

As samples for this assay, solutions with 500 ng/ml, 100 ng/ml and 10 ng/ml of a purified human thyroglobulin standard (Novo Industri A/S, Bagsvaerd, Denmark) in PBS-BSA were used. PBS-BSA without added thyroglobulin was used as a blank.

The device was opened and 25 μl of each sample was applied to spot 36 and the same volume of blank to spot 37. The extra lid provided to prevent evaporation was closed and the device was incubated for 30 min at room temperature. Then surface 35 was washed with approx. 1 ml PBS-Tween.

After washing, the device was closed by folding segment 32 upon segment 30 to transfer the conjugated antibody in absorbent pad 41 onto the plastic surface 35. The device was left closed and incubated for 30 min at room temperature.

The device was then reopened to expose surface 35, which was washed with approx. 1 ml PBS-Tween. Segment 31 was then folded onto segment 30 to transfer the chromogenic substrate in absorbent pad 39 onto plastic surface 35. The device was again left closed and incubated for 10 min at room temperature. The color reaction was then immediately read on the back of the device through the transparent plastic at spots 36 and 37. A faint yellow color was designated "+", a distinct yellow color "++" and a strong yellow color "+++".

Results

Human Thyroglobulin standards (in PBS-BSA)

| Concentration | | Reaction |
|---|---|---|
| 500 ng/l | 760 pmol/l | +++ |
| 100 ng/l | 150 pmol/l | ++ |
| 10 ng/l | 15 pmol/l | + |
| Blank | | − |

As can be seen, the device according to the invention was capable of providing semiquantitative analytical information at very low concentrations of the analyte.

Assay for feline leukemia virus

The assay of feline leukemia virus is important in veterinary practice to diagnose leukemia in cats.

Preparation of the device

Antibody was fixed to the plastic slide 35 by applying 50 μl of monoclonal anti-feline leukemia virus antibody (clone 1, Cambridge BioScience Corporation, Hopkinton, Mass., (U.S.A.) in a concentration of 10 μg/ml diluent, to each of spots 36 and 37. The diluent (abbreviated PBS) was 0.05 mol/l sodium phosphate, 0.15 mol/l NaCl, pH 7.2. The slides were incubated in a humidity chamber for 3 h at 37° C. They were then rinsed with approx. 10 ml washing solution (abbreviated PBS-Tween), consisting of 0.05% Tween ®-20 (Sigma Chemical Co., St. Louis, Mo., U.S.A.) in PBS. Thereafter the slides were submerged in a dish containing a solution (abbreviated PBS-BSA) consisting of 1% w/v bovine serum albumin (Sigma Chemical Co., St. Louis, Mo., U.S.A.) in PBS and incubated 60 min. at 37° C. Subsequently the slides were again rinsed with approx. 10 ml PBS-Tween, followed by 10 ml distilled water and left to dry.

The absorbent pad 41 was impregnated with a solution of peroxidase conjugated monoclonal anti-feline leukemia virus antibody (clone 2, Cambridge BioScience Corporation, Hopkinton, Mass., U.S.A.), diluted 1:5. The absorbent pad 39 was impregnated with a chromogenic substrate solution of 0.1% w/v 2,2'-azino-di-3-ethylbenzthiazoline sulfonate (Boehringer Mannheim GmbH, Mannheim, Germany), 0.15% $H_2O_2$ in 0.05 mmol/l sodium phosphate buffer, pH 6.0.

Execution of the assay

The assay was performed essentially as illustrated in FIG. 7 with sequences XX-XXVI. However, the following details of samples, volumes, times and other conditions may be added.

As samples for this assay, 10 actual serum samples from suspected cats were used. PBS-BSA was used as a blank.

The device was opened and 1 drop of approx. 50 μl of each sample was applied to spot 36 and the same volume of blank to spot 37. The device was then closed by folding segment 32 upon segment 30 to transfer the conjugated antibody in absorbent pad 41 onto the plastic surface 35. The device was left closed and incubated for 15 min at room temperature.

The device was then reopened to expose surface 35, which was washed with approx. 5 ml PBS-Tween. Segment 31 was then folded onto segment 30 to transfer the chromogenic substrate in absorbent pad 39 onto plastic surface 35. The device was again left closed and incubated for 2 min. at room temperature. The color reaction was then immediately read on the back of the device through the transparent plastic at spots 36 and 37. A faint green color was designated "+", a distinct green color "++" and a strong green color "+++". The assay results were compared to a commercially available test for feline leukemia virus (Pitman-Moore, Inc., Philadelphia, Pa., U.S.A.) run simultaneously in microtitration cups.

Results

| Sample number | Device according to the invention | Pitman-Moore procedure |
| --- | --- | --- |
| 1 | − | negative |
| 2 | − | negative |
| 3 | − | negative |
| 4 | + | negative |
| 5 | − | negative |
| 6 | − | positive |
| 7 | + | positive |
| 8 | +++ | positive |
| 9 | +++ | positive |
| 10 | +++ | positive |

The procedures were in agreement for 8 of the 10 samples tested. The diverging results for samples 4 and 6 may either have been caused by procedural factors or the clinical status of the samples.

What is claimed is:

1. A device for detecting a component in a sample, comprising:
   at least one reagent selected to react with a sample to form a product having a detectable substance,
   a detecting reagent selected to indicate the presence of the detectable substance,
   a continuous sheet having at least first and second segments,
   the first segment having a reaction site on which the at least one reagent is provided,
   the second segment having a detecting site on which the detecting reagent is provided,
   the first and second segments being foldably connected such that the reaction site may be brought into overlapping relationship with the detecting site,
   the continuous sheet being provided with means for removing one of the detectable substance and an unreacted fraction of the at least one reagent from the reaction site so that detectable substance may be reacted with the detecting reagent after separation of the detectable substance from an unreacted fraction of the at least one reagent,
   the continuous sheet being constructed from a single piece of cardboard.

2. The device according to claim 1, wherein said continuous sheet further comprises a third segment comprising an inhibiting site and an inhibitor for a detecting reaction, the third segment arranged on said continuous sheet so as to be foldable into contact with the second segment, whereby the detecting reaction may be inhibited.

3. The device according to claim 1, wherein the segments are foldable in overlapping relation to each other so as to form a package.

4. The device according to claim 1, for enzyme immuoassay based on antigen-antibody reactions, wherein the reaction site on the first segment is provided with a solid phase to which enzyme is chemically bound in the presence of antigen or antibody in the sample, and that the detecting site comprises an enzyme substrate that reacts with the enzyme which has not been chemically bound to the solid phase of the reaction site on the first segment.

5. The device according to claim 1, wherein the at least one reagent and said detecting reagent are selected for immuno chemical analysis.

6. The device according to claim 1, wherein the removing means includes a third segment of the continuous sheet having a separation medium, the third segment positioned on the continuous sheet so as to be foldable into an operative position in between the first and the second segments, whereby the detectable substance may be transferred to the detecting site from said reaction site through the separation medium.

7. The device according to claim 6 for use in analyses containing a separation of a fluid phase from a solid phase and detection of a substance in the fluid phase, wherein the first segment includes a container at the reaction site, the container containing a solid phase reagent, and having a covered opening for receiving a sample, the separation medium of the third segment passing the fluid phase but not the solid phase so that when the device is inverted the fluid phase can be brought into contact with the detecting reagent.

8. The device according to claim 7 wherein the detecting reagent is a color-generating reagent and the second segment contains means defining a window whereby the generated color may be observed, the segments being foldable in overlapping relation to each other so as to form a package.

9. The device according to claim 8 wherein the continuous sheet further comprises a fourth segment having an inhibiting site provided with an inhibitor for the detecting reaction, the fourth segment arranged on said continuous sheet so as to be foldable into contact with the second segment, whereby the detectng reaction may be inhibited.

10. A device for use in enzyme immunoassay based on antigen-antibody reactions, comprising a continuous sheet having first, second and third segments, the first segment having a reaction site, the second segment having a detection site, and the third segment having a third site, and means for removing an unreacted fraction of a reagent, wherein the reaction site includes a layer of transparent plastic with a first location for receiving a test sample and a second location for receiving a control sample, the layer of plastic being provided with a reagent in the form of one of an antibody and an antigen fixed thereto, the detecting site provided with a detecting reagent in the form of a chromogenic enzyme substrate, the third site provided with an absorbent pad containing soluble, enzyme-labelled antibody or antigen, whereby when the reaction site contains an antibody, the third site also contains an antibody and when the reaction site contains an antigen, the third site also contains an antigen, the third segment being position on the continuous sheet so as to be foldable into a position overlapping the first segment, whereby the third segment may be folded to overlap the first segment before the second segment is folded to overlap the first segment, and the removing means being in the form of absorbent material, placed in at least one well on the first segment, in such a way that when a washing liquid is applied to the transparent plastic on the first segment for washing away unreacted reagent before the third segment is folded to overlap the first one, said washing solution is automatically absorbed by the absorbent material.

11. A device for detecting a component in a sample, comprising:
   at least one reagent selected to react with a sample to form a product having a detectable substance,
   a detecting reagent selected to indicate the presence of the detectable substance,
   a continuous sheet having at least first and second segments,
   the first segment having a reaction site on which the at least one reagent is provided,
   the second segment having a detecting site on which the detecting reagent is provided,
   the first and second segments being foldably connected such that the reaction site may be brought into overlapping relationship with the detecting site,
   the continuous sheet being provided with means for removing one of the detectable substance and an unreacted fraction of said at least one reagent from the reaction site so that the detectable substance may be reacted with the detecting reagent after separation of the detectable substance from an unreacted fraction of the at least one reagent,
   wherein the continuous sheet is constructed from a single piece of plastic.

12. The device according to claim 11, wherein the continuous sheet further comprises a sample receiving segment arranged on the continuous sheet so as to be foldable to bring the sample into contact with any selected reagent on another segment.

13. The device according to claim 11, wherein the detecting reagent is a color-generating reagent and that one of the segments contains means defining a window whereby the generated color may be observed.

14. The device according to claim 11, for enzyme immunoassay based on antigen-antibody reactions, wherein the reaction site on the first segment is provided with a solid phase to which enzyme is chemically bound the presence of antigen or antibody to the sample and that the detecting site of the second segment comprises an enzyme substrate that reacts with the enzyme which remains chemically bound on the solid phase of the reaction site on the first segment after washing.

15. The device according to claim 11, for use in enzyme immunoassay based on antigen-antibody reactions, wherein the reaction site includes a layer of transparent plastic with a first location for receiving a test sample and a second location for receiving a control sample, the layer of plastic being provided with a reagent in the form of antibody or antigen fixed thereto, the detecting reagent comprising a chromogenic enzyme substrate, said continuous sheet further comprising a third segment having a third site provided with an absorbent pad containing a soluble, enzyme-labelled antibody or antigen whereby when the reaction site contains an antibody, the third site also contains an antibody and when the reaction site contains an antigen, the third site also contains an antigen, the third segment being positioned on the continuous sheet so as to be foldable into a position overlapping the first segment, whereby the third segment may be folded to overlap the first segment before the second segment is folded to overlap the first segment, and the removing means comprising absorbent material, placed in at least one well on the first segment, in such a way that when washing liquid is applied to the transparent plastic on the first segment for washing away unreacted reagent before the third segment is folded to overlap the first segment, the washing solution is automatically absorbed by the absorbent material.

16. The device according to claim 11, wherein the segments are foldable in overlapping relation to each other so as to form a package.

17. The device according to claim 11, wherein the removing means includes an absorption medium arranged adjacent the reaction site of the first segment so that washing liquid may be applied to the reaction site and removed from the reaction site by the absorption medium.

18. The device according to claim 17, for use in enzyme immunoassay based on antigen-antibody reactions, wherein the reaction site includes a layer of transparent plastic with a first location for receiving a test sample and a second location for receiving a control sample, the layer of plastic being provided with a reagent in the form of antibody or antigen fixed thereto, the detecting reagent comprising a chromogenic enzyme substrate, the continuous sheet further comprising a third segment having a third site provided with an absorbent pad containing soluble, enzyme-labelled antibody or antigen whereby when the reaction site contains an antibody, the third site also contains an antibody and when the reaction site contains an antigen, the third site also contains an antigen, the third segment being positioned on the continuous sheet so as to be foldable into a position overlapping the first segment, whereby the third segment may be folded to overlap the first segment before the second segment is folded to overlap the first segment.

19. The device according to claim 17, wherein the first segment includes a hollowed portion open to the reaction site, and said absorption medium arranged in the hollowed portion such that when a washing solution is applied to the reaction site for washing away the unreacted fraction, the washing solution is absorbed into the hollowed portion.

20. The device according to claim 19, for use in enzyme immunoassay based on antigen-antibody reactions, wherein the reaction site includes a layer of transparent plastic with a first-location for receiving a test sample and a second location for receiving a control sample, the layer of plastic being provided with a reagent in the form of antibody or antigen bound thereto, the detecting reagent comprising chromogenic enzyme substrate, the continuous sheet further comprising a third segment having a third site provided with an absorbent pad containing a soluble, enzyme-labelled antibody or antigen, the third segment being positioned on said continuous sheet so as to be foldable into a position overlapping the first segment, whereby the third segment may be folded to overlap the first segment before the second segment is folded to overlap the first segment.

21. The device according to claim 20 wherein the detecting reagent is a color-generating reagent and that the first segment contains means defining a window, whereby the generated color may be observed, the segments being foldable in overlapping relation to each other so as to form a package.

22. A device for detecting a component in a sample, comprising:
at least one reagent selected to react with a sample to form a product having a detectable substance,
a detecting reagent selected to indicate the presence of the detectable substance and,
a continuous sheet having at least first and second segments, wherein
the first segment having a reaction site on which the at least one reagent is provided,
the second segment having a detecting site on which the detecting reagent is provided,
the first and second segments being foldably connected such that the reaction site may be brought into overlapping relationship with the detecting site, and
the sheet being provided with means for removing one of said detectable substance and an unreacted fraction of said at least one reagent from the reaction site so that the detectable substance may be reacted with the detecting reagent after separation of the detectable substance from an unreacted fraction of the at least one reagent,
wherein the at least one reagent and said detecting reagent form a material for biochemical analysis, selected from the group consisting of enzyme immunoassay, fluorescence immunoassay, luminescence immunoassay and analysis based on hybridization reactions between nucleic acids.

23. A device for detecting a component in a sample, comprising:
a continuous sheet having first, second and third segments;
a reaction site provided on the first segment;
a first reagent provided at the reaction site;
second reagent means provided at the reaction site for reacting with at least one of the first reagent and a component to bind a detectable substance to at least one of the reaction site and the first reagent in the presence of the component in a sample;
separating means provided on the second segment for separating any unbound detectable substance from the bound detectable substance; and
means provided on the third segment for detecting any separated unbound detectable substance;
the first, second, and third segments being foldably connected to that the reaction site can be brought into overlapping relationship with the second and third segments.

24. The device according to claim 23, further comprising a fourth segment on the continuous sheet, the fourth segment containing means for inhibiting a detecting reaction.

25. The device according to claim 23, wherein the separating means comprises filter paper.

26. The device according to claim 25, wherein the first reagent is bound to a solid phase at the reaction site that can not pass through the filter paper.

27. A device for detecting a component in a sample, comprising:
a continuous sheet having first, second, and third segments;
a reaction site provided on said first segment;
a first reagent chemically bound to the reaction site;
a second reagent means provided on said second segment for reacting with at least one of the first reagent and a component in a sample to bind a detectable substance to the reaction site in the presence of the component in the sample;
the reaction site being provided such that any unbound detectable substance may be removed from the reaction site; and
a detecting reagent provided on the third segment for detecting any detectable substance bound to the reaction site;
said first, second, and third segments being foldably connected so that the reaction site can be brought into overlapping relationship with the second and third segments.

28. The device according to claim 27, wherein the first reagent is one of an antibody and an antigen that is able to bind with the component in the sample.

29. The device according to claim 28, wherein when the first reagent is an antibody, the second reagent means is a labelled antibody that is able to bind with the first reagent and component complex.

* * * * *